United States Patent
Böhm et al.

(10) Patent No.: US 8,977,015 B2
(45) Date of Patent: Mar. 10, 2015

(54) METHOD FOR DETERMINING A POSITION FOR AT LEAST ONE SEMI-TRANSPARENT DIAPHRAGM AND ASSOCIATED FACILITY

(75) Inventors: Stefan Böhm, Oberasbach (DE); Klaus Finkler, Spardorf (DE)

(73) Assignee: Siemens Aktiengesellschaft, München (DE)

( * ) Notice: Subject to any disclaimer, the term of this patent is extended or adjusted under 35 U.S.C. 154(b) by 2142 days.

(21) Appl. No.: 12/008,942

(22) Filed: Jan. 15, 2008

(65) Prior Publication Data
US 2008/0175462 A1    Jul. 24, 2008

(30) Foreign Application Priority Data

Jan. 17, 2007  (DE) .................. 10 2007 002 417

(51) Int. Cl.
| | |
|---|---|
| G06K 9/00 | (2006.01) |
| A61B 6/06 | (2006.01) |
| A61B 6/00 | (2006.01) |
| G06T 7/00 | (2006.01) |
| H04N 5/32 | (2006.01) |

(52) U.S. Cl.
CPC ............... *A61B 6/06* (2013.01); *A61B 6/4441* (2013.01); *A61B 6/542* (2013.01); *G06T 7/0042* (2013.01); *G06T 7/0083* (2013.01); *G06T 2207/10121* (2013.01); *G06T 2207/20036* (2013.01); *G06T 2207/30004* (2013.01); *H04N 5/32* (2013.01)
USPC .......................... 382/128; 382/130; 382/131

(58) Field of Classification Search
USPC ................. 382/128, 130, 131, 132; 128/922; 378/40, 62, 87, 176
See application file for complete search history.

(56) References Cited

U.S. PATENT DOCUMENTS

| 4,817,125 A | 3/1989 | Sklebitz |
| 6,330,299 B1 * | 12/2001 | Curtis et al. ................... 378/62 |
| 6,373,918 B1 * | 4/2002 | Wiemker et al. ................ 378/62 |
| 2003/0053674 A1* | 3/2003 | Armato et al. ................ 382/132 |
| 2005/0232397 A1* | 10/2005 | Atzinger et al. .............. 378/163 |

FOREIGN PATENT DOCUMENTS

| DE | 36 21 868 A1 | 1/1988 |
| DE | 199 11 587 A1 | 9/2000 |
| DE | 10 2004 060 127 A1 | 6/2006 |

* cited by examiner

*Primary Examiner* — Nicole Ippolito

(57) ABSTRACT

The invention relates to a method for determining a position for at least one semi-transparent diaphragm during a radiological observation of a body region of a patient by means of a radiological facility, in particular during an observation accompanying an interventional measure, comprising: producing at least one radiological image recording and/or a sequence of image recordings by means of the radiological facility; analyzing the image recording and/or the sequence of image recordings by means of automatic image processing by a computing facility for identifying less absorbent image regions which may be present; and automatically determining the position for the at least one semi-transparent diaphragm as a function of the image analysis result by means of the computing facility.

19 Claims, 6 Drawing Sheets

METHOD FOR DETERMINING A POSITION FOR AT LEAST ONE SEMI-TRANSPARENT DIAPHRAGM AND ASSOCIATED FACILITY

CROSS REFERENCE TO RELATED APPLICATIONS

This application claims priority of German application No. 10 2007 002 417.9 filed Jan. 17, 2007, which is incorporated by reference herein in its entirety.

FIELD OF THE INVENTION

The invention relates to a method for determining a position for at least one semi-transparent diaphragm during a radiological observation of a body region of a patient by means of a radiological facility, in particular in the event of an observation accompanying an interventional measure, as well as an associated facility.

BACKGROUND OF THE INVENTION

Manipulations using a catheter, a guide wire and similar such medical instruments are often carried out in the field of interventional radiography and/or radiology on a human or animal patient, during which manipulations an accompanying imaging observation or monitoring is required and/or desired. To this end, an x-ray fluoroscopy for observing a relevant body region is carried out in parallel for instance.

It may be problematical here that large intensity differences may occur in the images produced in the case of recordings in the region of the heart for instance but also in the case of recordings in other body regions. The reason for this is that extremely x-ray-transparent regions and organs such as lungs for instance are also located in the image region radiated by means of the x-rays in addition to the intensely absorbent organs or tissue structures such as the heart or spinal column. The consequences thereof consist in very large dose differences within the relevant image region, thereby resulting if applicable in the image recording detector and the image system being overcontrolled.

The dose differences adversely affect the image quality, so that very dark and low contrast in addition to extremely light or even over-radiated regions are found. To counteract this problem, semi-transparent diaphragms are used since the transition between the regions with a high absorption and those with a low absorption is mostly very sharp and linear, said semi-transparent diaphragms being positioned over the less absorbent region. In this way, the dose difference relative to the highly absorbent region is reduced and the overall dynamic level of the image region is thus minimized.

The positioning of these semi-transparent diaphragms, which are used to control dose differences, is carried out manually. To this end, joysticks are used for instance, while a live observation of the manual positioning process is carried out on a monitor.

The manual positioning of the diaphragm requires a certain degree of experience and is comparatively complicated because each time a new positioning has to be carried out for instance, when individual parameters such as the table position, the angulation, a zoom stage or the position of the patient is changed. Accordingly, less time and/or attention is available to medical personal for medical actions or to technical personal for the actual image recording action, in other words the monitoring of a quality of the image recordings which is in all other cases sufficient. The operator, in this case a technician or scientist who operates a radiological facility, or also a doctor and/or medicine-related assistant who hereby deals with the implementation of the interventional method or any other medical measure, is solely responsible for the diaphragm positioning.

SUMMARY OF THE INVENTION

The object underlying the invention thus consists in specifying a method for determining a position for at least one semi-transparent diaphragm, which is improved in this regard.

To solve this, a method of the type mentioned in the introduction is provided, comprising the following steps:
  Producing at least one radiological image recording and/or a sequence of image recordings using the radiological facility,
  Analyzing the image recording and/or the sequence of image recordings using automatic image processing by means of a computing facility for identifying less absorbent image regions which are present if applicable and automatically determining the position for the at least one semi-transparent diaphragm as a function of the image analysis result by means of the computing facility.

With the method according to the invention, it is thus no longer necessary for a user, such as a technician and/or doctor or medical staff, to have to manually position a semi-transparent diaphragm in order to control the intensity differences in the radiological recordings. Instead, a suitable, at best the optimal position for a diaphragm of this type is automatically determined.

To this end, image recordings are firstly produced within the scope of the monitoring, with it being possible for these to be a single or a number of single images or also a film or video.

These image recordings and/or the film of image recordings are automatically analyzed by a computing facility in order thus to identify the less absorbent image regions, in other words essentially x-ray-transparent image regions. The less absorbent regions indicate an absorption below a threshold value for instance in order to be classified as such on the part of the computing facility.

The identification of such less absorbent image regions finally allows the optimum position for one or a number of semi-transparent diaphragms to be automatically determined on the part of the computing facility using corresponding image processing and/or software. The diaphragm can then be arranged at the determined position, in order thus to counteract overcontrolling as a result of high dose differences.

The radiological observation may be a conventional radiography process, but may also be a modem radiological method such as computer tomography or suchlike.

The method according to the invention for determining the diaphragm position only relates to the technical method of an optimum image recording without quality losses. The medical measures carried out if necessary in parallel, in other words the intervention by means of a catheter or such like for instance, is not included in the present method. The method can be carried out completely automatically or accompanied and/or monitored by means of a technician or scientist, who deals with the image recording.

To ensure that the method can be carried out in an error-free fashion, the image recordings to be analyzed must be standardized. This means that the image recordings are to be produced using a dose regulation and an automatic electronic amplification controller is to be activated if applicable. This ensures that the highly and less absorbent objects in the image region always generate the same gray scale value ranges. A further image analysis for dynamic reduction or noise reduction or such like can if necessary be associated herewith.

A control facility for activating at least one actuator provided for adjusting the position of the semi-transparent diaphragm can be controlled in accordance with the invention as a function of the determined position. It is thus also possible automatically to correctly adjust the suitable diaphragm position, which was automatically determined, by means of correspondingly activating one or a number of actuators for the adjustment of the position of the diaphragm. Faults which may arise as a result of manually adjusting the automatically determined position are thus avoided.

For the purpose of this control of the diaphragm position, the automatically determined position can be transferred from the computing facility to the control facility for the actuators. It is similarly possible for the actuators to be directly controlled by the computing facility, which has also determined the position of the diaphragm. Finally, an automatic adjustment of the position of one or a number of diaphragms for an optimum accompanying image recording or overall for a radiological image generation is possible without further fault sources.

In accordance with the invention, the image analysis for identifying less absorbent image regions can comprise at least the following steps:
  binarization of the image recording and/or the sequence of image recordings by specifying a threshold value and
  Analyzing the binarized image recording and/or the binarized sequence of image recordings in respect of the appearance of edges.

Within the scope of the binarization, all pixels which lie above a threshold value which is predetermined on the part of a user, if necessary by inputting prior to the image recording, and/or by means of software, are set to 1, whereas all pixels below the threshold value are assigned to the value 0.

In case of doubt, a threshold value which lies at half of the maximum gray scale value is suitable. A rough isolation and/or identification of the pixels belonging to the less absorbent regions with high gray scale values can thus be achieved.

After binarizing the image recording and/or the film from consecutive recordings and other image sequences, an analysis relating to the appearance of edges is carried out, in other words in respect of the appearance of transitions between high and less absorbent image regions. The transitions between 0 and 1 and/or 1 and 0 in the binarized image are thus identified for instance by means of a software package for the automatic image processing, which is stored on the computing facility.

Furthermore, the following step can be carried out following the binarization:
  Morphological filtering of the image recording and/or the sequence of image recordings in order to eliminate flaws and/or gaps.

This thus concerns compensating for image faults, be they individual flaws or larger gap regions. The aim is to achieve the most homogenous surface of the less absorbent region as possible. To this end, different morphological filter methods can be used, wherefor the use of a so-called closing function is worth mentioning for instance, in which a dilatation and as a result an erosion are carried out, in other words with the use thereof corresponding surrounding areas are taken into account in respect of the value of a central pixel to be set.

In accordance with the invention, the analysis in respect of the appearance of edges can comprise at least one, preferably all, of the following steps:
  Edge detection by means of an edge filter,
  Elimination of edges produced if applicable by one or a number of non-transparent diaphragms and
  Transformation of the image recording and/or the sequence of image recordings in the Hough space.

The analysis is preferably carried out by implementing these steps in said sequence. By default, a sequence of the method according to the invention can thus be seen in that after the production of the image recordings, these are binarized, the binarized images are filtered and an edge detection is then carried out. Subsequently, the edges produced by regular superimposition, in other words edges, which are produced by (fixed) non-transparent diaphragms, are eliminated. Such non-transparent totally absorbent diaphragms do not need to be positioned, but are as a rule generally fixed in position at the start of the image recording so that the edges produced by the diaphragms have an interfering effect for position determination methods according to the invention.

After eliminating the edges produced by regular superimposition, a transformation of the image recording and/or the film or suchlike takes place in the Hough space, in order to allow geometric forms to be recognized, here particularly the edges and/or lines in the image.

A suitable edge filter is expediently used for edge detection, which only provides a signal at the points at which a transition between 0 and 1 and/or 1 and 0 exists. Suitable filters are Sobel filters or Roberts filters for instance.

All aforementioned steps need not nevertheless necessarily be carried out. By way of example, the elimination of regular edges can then be dispensed with if no non-transparent diaphragms are present and/or the image analysis can be restricted to one region without such diaphragms. Furthermore, the edge detection can if necessary be completed by another transformation and/or another method for identifying geometric forms as an alternative to the Hough transformation.

To delete or eliminate edges produced by non-transparent diaphragms, edges running in parallel to the image border can be deleted in accordance with the invention. These fixed diaphragms are herewith generally run in parallel to the image borders. Their edges must be eliminated so that they do not have an interfering affect on the further image analysis. To this end, a scanning of all columns and/or lines is if necessary carried out after the gray scale value 1 first appears from all four image borders. If a column and/or line with a gray scale value equal to 1 is discovered, all pixels of the corresponding column or line are set to 0. In addition, all pixels of a specific number n of further columns or lines at the image centre are likewise set to 0. The number n of further columns or lines likewise to be set to 0 at the image centre can be different, with this number depending in particular on the image matrix size. By way of example, a suitable value of n=20 for an image matrix variable of 960*960 is worth mentioning. In the case of different image sizes or as a function of the recording region, completely different numbers, in particular also different numbers for the different edges, can however also be suitable.

This elimination method allows edges which run parallel to the image border which are to be assigned to the edges produced by means of regular superimposition to be reliably deleted, whereas non-parallel edges which can be attributed to extreme dose differences in the case of a cardiological recording for instance, remain.

The Hough transformation can be carried out if only one or a number of edges is still located in the edge image, after eliminating the edges which are produced by fixed diaphragms for instance, said edges being produced by a transition from a highly to a less absorbent region.

It is also possible for a further edge to be located in the image, in the case of the relevant image and/or image sequence which is to be analyzed, said edge being produced by a semi-transparent diaphragm, which was already at least partially moved into the image region while the image recording and/or the video sequence or the film was produced.

To analyze a sequence of image recordings, these can be combined if necessary and specific averaging methods used. There can also be a preceding comparison of the individual images of the sequence in order, if applicable, to exclude specific images of the sequence from the analysis as a function of the comparison result or in order to only consider certain specifically relevant or temporally distanced images.

If the Hough transformation is now carried out, the lines of the image space are mapped onto peaks and/or clusters in the so-called Hough space. The coordinates of the peaks or clusters in the Hough space are then analyzed, in order to read off the angle and the normal distance of the corresponding line from the image centre point. In this way, the Hough space is designed such that the respective angle is specified on the horizontal axis, whereas the vertical axis reproduces the normal distance from the image centre point.

The method for determining a position for at least one semi-transparent diaphragm can also comprise the following steps:

low pass filtering of the image recording and/or the sequence of image recordings transformed by means of a Hough transformation in the Hough space, search for local maxima in the image recording transformed in the Hough space and/or the sequence of image recordings and determining the position for the semi-transparent diaphragm on the basis of the local maxima in the image recording transformed in the Hough space and/or the sequence of image recordings.

The low pass filtering of the Hough image has the background such that depending on how high the level of linearity of the identified edge is, a corresponding cluster in the Hough space concentrates on a single point. In the opposite case, the cluster divides and/or smudges in the Hough space all the more, the more the underlying edge deviates from a straight line, with such deviations generally being anticipated during the region transitions sought.

It is thus essential to avoid secondary maxima, which can be generated by short or straight line segments. To this end, the low pass filtering is carried out. For instance, an averaging filter with a specific expansion of some pixels in the horizontal and vertical direction can be used for instance within the scope of the low pass filtering. The expansion of the filter is to be suitably selected here as a function of the image recordings to be used to observe the interventional measures. By way of example, the use of an averaging filter with an expansion of 11 pixels in the horizontal and vertical direction for an image matrix variable of 960*960 is mentioned, which has proven to be suitable with this image size. The local maxima in the Hough space, which should in turn be larger than a specific threshold value which can be adjusted or predetermined on the part of a user and/or software stored on the computing facility, is sought. This threshold value can be selected suitably. With the aforementioned image matrix variable, a threshold value of 30 can be optimal for instance.

A search for the global maximum alone is not sufficient since more than one, in particular two edges can be in the image e.g. by means of semi-transparent diaphragms which have already been partially moved therein.

The method for locating local maxima can proceed such that the global maximum, which simultaneously corresponds to the first local maximum, is initially sought. As a result, all pixels in an n*n environment about this global maximum are set to 0. The n*n environment used here can in turn be suitably selected, with it being possible for a value of n equal to 50 for instance to be suitable with an image matrix size of 960*960.

If the global maximum is now sought a second time, this corresponds to the second local maximum. The sought end position for the semi-transparent diaphragm is then the local maximum, which lies in the vicinity of the image centre point. This position can be read from the vertical axis of the Hough image.

Following the successful search for the local maxima, the position for the semi-transparent diaphragm can thus be obtained from the Hough image by determining the angle and/or the position, given by the standard distance from the image centre point.

Alternatively, a fit method can be carried out for identifying straight lines and/or lines, if no Hough transformation is to be used. Such a fit method can also be used in addition to a Hough transformation, for monitoring the results for instance.

The method can also be advantageously carried out in that the position for the semi-transparent diaphragm is determined on the basis of an image recording and/or a sequence of image recordings, which comprise a semi-transparent diaphragm which is at least partially moved into the recording region or comprise no semi-transparent diaphragm which is moved therein. Different possibilities for position determination thus exist. The position determination can be carried out without a diaphragm already being located in the image recording space, as a result of which the diaphragm is then automatically moved in for instance by means of the controlled actuators. Furthermore, one or a number of semi-transparent diaphragms can already be wholly or partially located in the image recording space. In this case, a henceforth better position can be determined for these diaphragms or positions for other diaphragms can be determined.

The already moved-in diaphragms do not interfere with the method for determining the optimal position for these diaphragms and/or one of these diaphragms, if this is carried out as previously illustrated. Instead, an optimum positioning of the diaphragms already located in the image space can be advantageously achieved using the method for further recordings to be carried out in sequence.

The position for the semi-transparent diaphragm can be determined on the basis of a highly dynamic sequence of image recordings. The position for the semi-transparent diaphragm can thus be determined from moving images. A film can thus be used for instance for the analysis, a film in the field of cardiology, on which the heart movement is shown. The image recordings can also show further dynamic processes, without these movement processes, such as the breathing for instance, negatively affecting the diaphragm positioning.

When reference is made to a highly dynamic instances, this term cannot be summarized in clear figures. By way of example, reference is only made to cardiology, in which a heart beat with a duration of approximately one second is considered, which breaks down into individual phases with a duration in sub seconds and/or tenths of seconds.

The position for the semi-transparent diaphragm can be determined in real time. The method can thus be carried out such that a position determination is carried out for each image and/or for each n'th image, whereupon the diaphragm is newly positioned provided this is necessary. It is thus advantageous that the positioning of the diaphragm of each change in the geometric ratio, for instance by movements of organs of suchlike, can be carried out in real time. Furthermore, the movement and/or actual position change of the diaphragm can be considered on the basis of a preceding analysis and corrections can be implemented if applicable.

The radiological observation can in particular be carried out in the field of cardiology, in which catheter interventions and other operations using medical instruments, which require a precise accompanying observation, are frequently carried out.

With a sequence of image recordings, the position for the semi-transparent diaphragm can only be jointly determined for some image recordings of the sequence and/or within the scope of an averaging for a number of image recordings.

For the position determination, each n'th image can thus be used and/or an averaging can be carried out by way of a specific number of images. It is also possible for the consideration of each n'th image and/or the averaging to be carried out alternately, depending on which phase the interventional measure to be observed for instance, which is implemented in parallel with the image recording, is located.

To determine the position for the semi-transparent diaphragm with a sequence of image recordings, a change in the determined position can if applicable be at least partially filtered out again over the course of the image sequence. A certain inertia can thus be imposed on the method if necessary, for instance if it emerges that a constant or very frequent repositioning of the diaphragm is not necessary and/or a change in the position, which was determined, is not relevant for the further process. A further filter can thus be used in the case of highly dynamic recordings, in order to avoid unnecessary and abrupt position changes, which can be disadvantageous for the further image recordings.

The analysis of the image recording and/or the sequence of image recordings can be carried out taking account of specifications by a user. In particular, a scientist familiar with the accompanying image recording, a physician for instance or a technician, can input values for suitable simulation parameters for instance for the search for the maxima in the Hough space or suchlike prior to or during the image recordings in order to optimize an otherwise automatically occurring analysis. It is also conceivable that a selection of filters is shown to the user or suchlike for an edge detection for instance, which can be expediently implemented in different fashions depending on the field of application and/or the recording region in the cardiology or in other regions.

The input and/or selection can be carried out here on the basis of a software interface on the computing facility and/or a further workstation.

Furthermore, the invention relates to a facility for implementing a method for determining a position for at least one semi-transparent diaphragm during a radiological observation of a body region of a patient, in particular such as is illustrated above, having a radiological facility for producing at least one radiological image recording and/or a sequence of image recordings with the radiological observation and a computing facility for analyzing the image recording and/or the sequence of image recordings in order to identify less absorbent image regions by means of an automatic image processing and for automatically determining the position for the at least one semi-transparent diaphragm as a function of the image analysis result.

The facility, which allows the position determination for semi-transparent diaphragms for an observation by means of radiological recordings, thus has a radiological facility for producing the image recordings as well as a computing facility for the necessary analysis. The radiological facility can be a C-arm system for instance. A computer tomography facility as a radiological facility is also conceivable. The computing facility comprises an image processing software in order to suitably analyze the image recordings and/or films. The image processing software can be designed here in the form of a software package. This software package can offer a user different options for an edge detection or a general parameter selection for instance and/or runs automatically following selection of a specific program.

The manual positioning of semi-transparent diaphragms is thus omitted in accordance with the invention so that errors herewith occurring are not able to negatively affect an interventional measure, which is implemented concomitantly with the radiological observation.

BRIEF DESCRIPTION OF THE DRAWINGS

Further advantages, features and details of the invention result from the following exemplary embodiments as well as with reference to the drawings, in which.

DETAILED DESCRIPTION OF THE INVENTION

Figure 1:
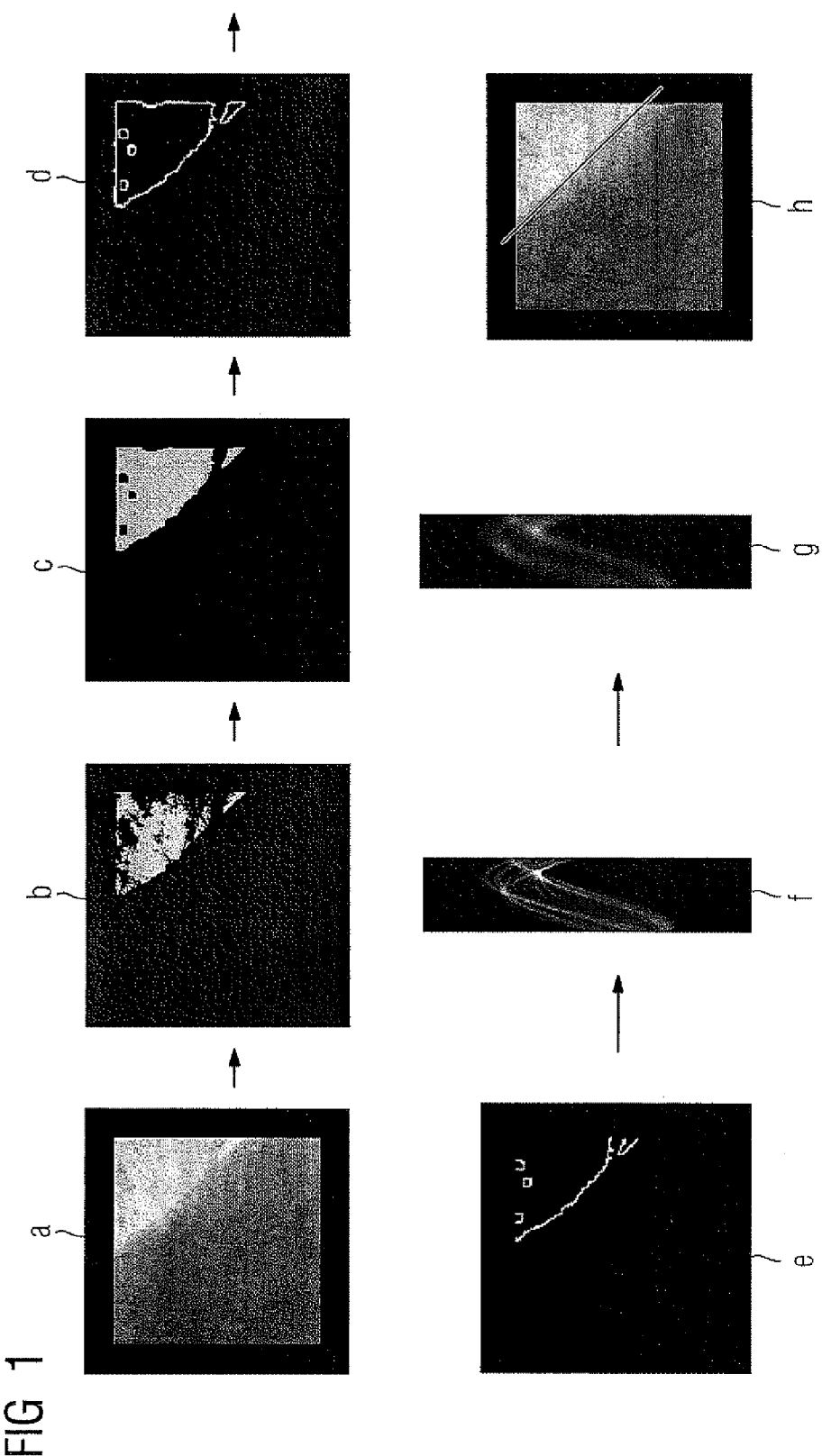
FIG. 1 shows a flow chart of a method according to the invention.

FIG. 1 shows a flow chart of a method according to the invention.

In step a, an image recording is first present, which was recorded within the scope of monitoring concomitantly provided for an interventional measure. This output image shows very large dose differences, in other words extremely dark, low contrast and extremely light image regions. The transition between these image regions is comparatively sharp and linear.

In the following step b, a binarization of the image recording is carried out in accordance with the inventive method, by setting pixels above a threshold value to 1 and setting pixels below a threshold value to 0. The threshold value is used as a threshold value which corresponds to half of the maximum gray scale value.

The filtering of the image binarized in step b is associated with the binarization in step c. A morphological filtering is used to eliminate flaws and gaps in the binarized image. This results in a predominantly homogenous surface of the less absorbent region. The filtered binary image is subjected to an edge detection in accordance with step d, so that a signal remains only at the points at which a transition from 0 to 1 and/or 1 to 0 is present.

In step e, edges produced finally be means of regular superimposition, which run in parallel to the image borders, are eliminated.

A Hough transformation according to step f follows this, by means of which the lines of the image of step e are mapped onto peaks and/or clusters in the Hough space. The Hough image produced is subjected to a low pass filtering in accordance with step g, in order to identify secondary maxima, which are generated by short straight line segments.

Step h finally shows the determined position into which the semi-transparent diaphragm for optimizing the image recordings to be recorded during the observation is to be introduced.

The following FIG. 2A-10A each show the situation, without a semi-transparent diaphragm being located in the image region. FIG. 2B-10B each show the situation with a partially moved-in semi-transparent diaphragm and/or FIG. 10B shows the situation with the semi-transparent diaphragm moved in at the correct position.

Figure 2A:
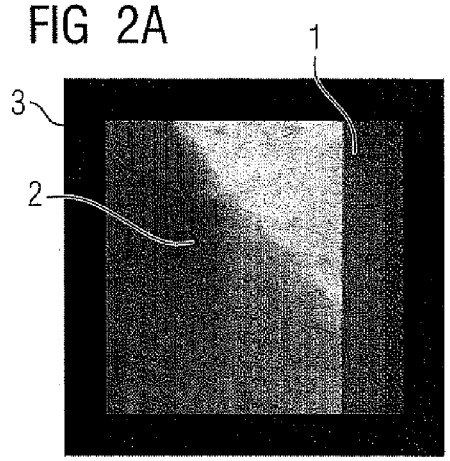
FIGS. 2A and 2B show output image recordings without and/or with a partially moved-in semi-transparent diaphragm.

FIG. 2A shows an output image recording, without a semi-transparent diaphragm being located in the image. A large intensity difference between a less absorbent image region 1 and a highly absorbent image region 2 is clearly visible. The transition between the two image regions 1 and 2 is determined in a comparatively sharp fashion. Fixed diaphragms are positioned on the image border 3 and/or in the assigned recording region. The present image recording is an image recording from the field of cardiology, in which interventional measures to be monitored, such as catheter examinations and suchlike for instance, are frequently carried out by means of image recordings.

Figure 2B:
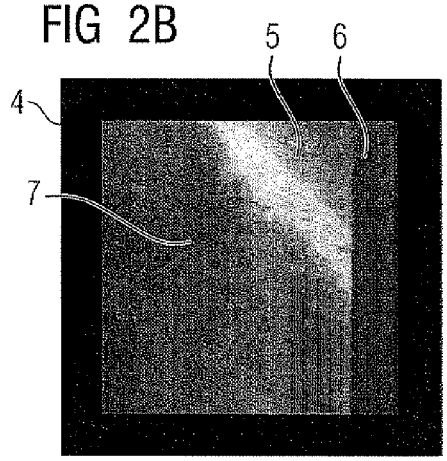

FIG. 2B shows the output image recording with a partially moved-in semi-transparent diaphragm, with dark areas in turn appearing on the image borders 4 as a result of fixed diaphragms which are not transparent. In addition to a smaller less absorbent image region 5, the partially moved-in semi-transparent diaphragm produces a new highly absorbent region 6, which is produced by the diaphragm. The highly absorbent image region 7 corresponds to the highly absorbent image region 2 of the output image recording of FIG. 2A without the moved-in diaphragm.

Figure 3A:
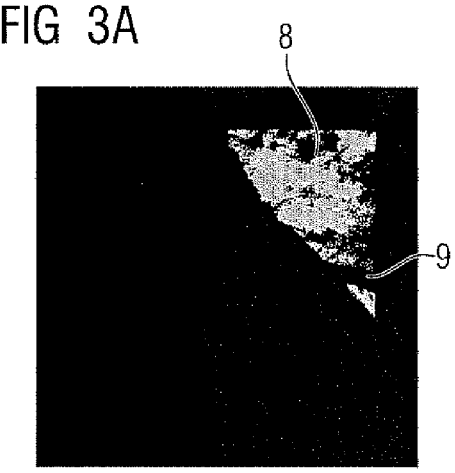
FIGS. 3A and 3B show the result of the binarization of the output image recording of FIG. 2A and 2B, FIGS. 4A and 4B show the result of the filtering of the binarized image recording as claimed in FIGS. 2A and 2B, FIGS. 5A and 5B show the respective image recording after an edge detection.

FIG. 3A shows the result of a binarization of the image recording of FIG. 2A without an inserted diaphragm. The pixels 8 above the set threshold value as well as the pixels 9 below the threshold value, which were set to 0 and are shown dark, are visible. An isolation of the pixels associated with the less absorbent regions with high gray scale values thus results.

Figure 3B:
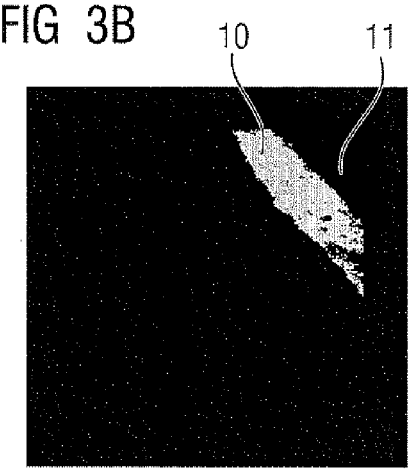

FIG. 3B shows a smaller number of pixels 10 above the threshold value in comparison with the pixels 11 below the threshold value by means of the already partially moved-in semi-transparent diaphragm, with the higher number of pixels below the threshold value being produced by means of the semi transparent diaphragm which is already partially moved into the top right of the image recording.

Figure 4A:
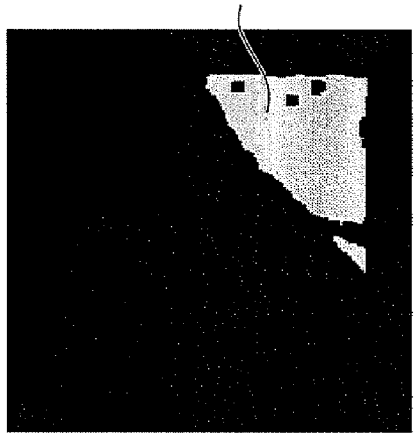
Figure 4B:
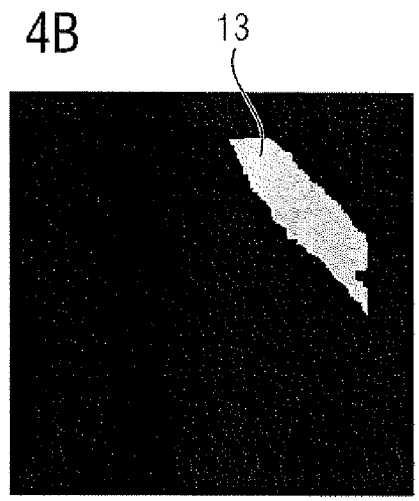

FIG. 4A and/or 4B show the result of the filtering of the binarized image of FIG. 3A and/or 3B without or if applicable with a partially moved-in semi-transparent diaphragm. The filtering is carried out using a morphological filter, as a result of which a comparatively homogenous surface 12 and/or 13 of the less absorbent region is produced. For filtering purposes, a closing function is used with a dilatation followed by an erosion.

Figure 5A:
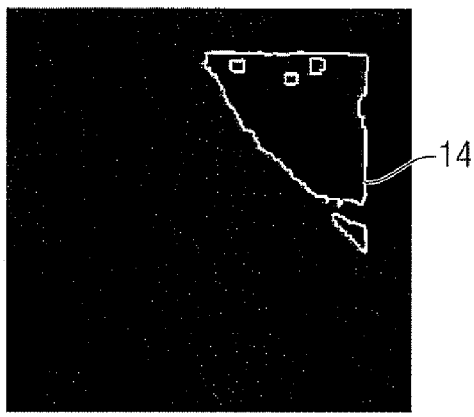
Figure 5B:
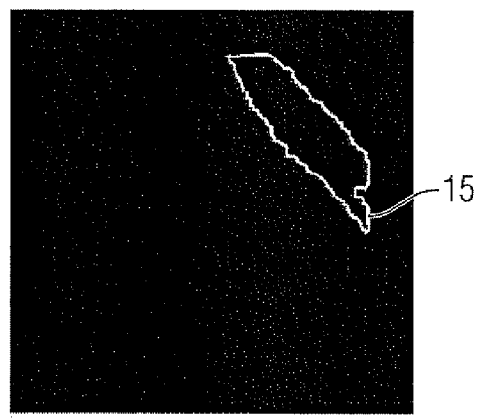

An edge detection according to FIGS. 5A and 5B follows hereon. This edge detection only supplies a signal at the points at which a transition between 0 and 1 and/or 1 and 0 is established. The edges 14 and/or 15 of FIGS. 5A and 5B herewith result. As a result of the already partially moved-in semi-transparent diaphragm in FIG. 5B, the edge running in parallel in each instance to the image periphery is inter alia missing in the right upper region, said edge being produced by means of the fixed diaphragm.

Figure 6A:
FIGS. 6A and 6B show the image recording after elimination by means of regular superimposition or the produced edges without and with a partially moved-in semi-transparent diaphragm.

FIG. 6A and/or 6B illustrate how the edges produced by regular superimposition have been eliminated in comparison with FIG. 5A and/or 5B. These edges appear as a result of non-transparent, in this sense regular, diaphragms in the image, which as a rule run parallel here to the image borders and are arranged in a fixed manner. To ensure that these edges do not interfere with the further image analysis, they are eliminated by a search in all columns and/or lines for a first appearance of the gray scale value 1 which was started from the four image borders. After locating such a column and/or line, all pixels of the corresponding column and/or line are set to 0. This can also be implemented for all pixels of n further columns or lines at the image center point. In this way, edges running in parallel to the image border are deleted, while non-parallel edges remain the same.

Figure 6B:
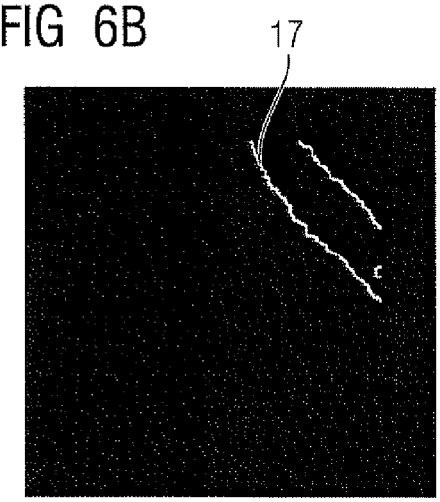
Figure 7A:
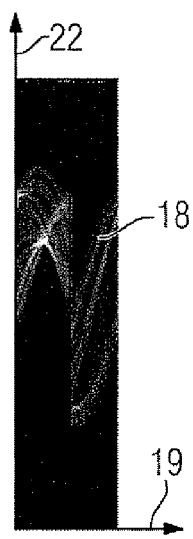
FIGS. 7A and 7B show the result of a Hough transformation of the image recording.
Figure 7B:
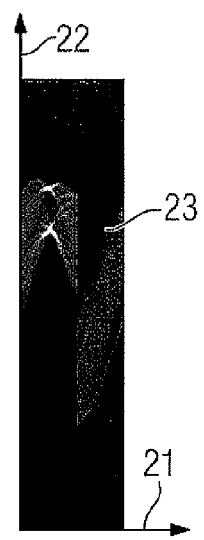

This results in image recordings, as are shown in FIGS. 6A and 6B for instance, which only comprise edges 16 and 17 which do not run parallel to the image borders. A Hough transformation according to FIGS. 7A and 7B is associated herewith. Edges running randomly in parallel to the edge further toward the image centre were not removed within the scope of the elimination. Only the edges which are specified by the transition from the high to the less absorbent region are located in the edge images.

If a semi-transparent diaphragm is already in the image, this likewise produces an edge, which can be seen in the edge image according to FIG. 6B.

As a result, the image is now transformed in the Hough space, as a result of which a representation is produced as in FIGS. 7A and 7B. The lines in the image space are mapped onto peaks and/or clusters in the Hough space. The angle and the normal distance from the image centre point of the line can be read off from the associated coordinates. The corresponding peaks and clusters 18 are shown in FIG. 7A for the instance without any moved-in semi-transparent diaphragm. In this way, the associated angle is plotted on axis 19, while the distance from the image centre point is plotted on axis 20.

Accordingly, FIG. 7B shows the instance of a partially moved-in semi-transparent diaphragm, the angle is plotted on axis 21 and the distance from the image centre point is plotted on axis 22. With the peaks and clusters 23 of FIG. 7B, the regions to be attributed to edges which were already covered by the partially moved-in semi-transparent diaphragm, are missing. The peaks and clusters 23 of FIG. 7B thus concentrate more clearly on the two clusters, which are to be assigned to the parallel edges in FIG. 6B.

Figure 8A:
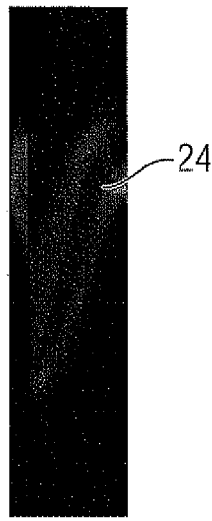
FIGS. 8A and 8B show the low pass filtered Hough image.
Figure 8B:
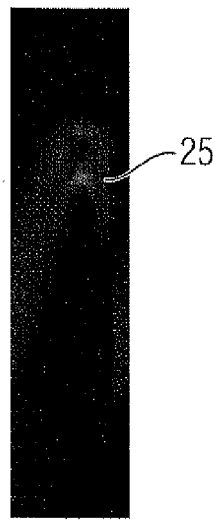

FIGS. 8A and 8B show the low pass filtered Hough images in each instance, which are produced from the Hough images in FIGS. 7A and 7B. The respective clusters 24, 25, which remain after the low pass filtering, can be seen. The background of the filtering is that a cluster 24, 25 in the Hough space concentrates all the more on an individual point, the higher the level of the edge underlying the linearity is. Blurring of the two clusters 24 and 25 is produced as a result of deviations from a straight line. Secondary maxima, which can be generated by large straight line segments, are thus avoided.

Figure 9A:
FIGS. 9A and 9B show the result, after which the global maximum of the Hough image is set to 0.
Figure 9B:
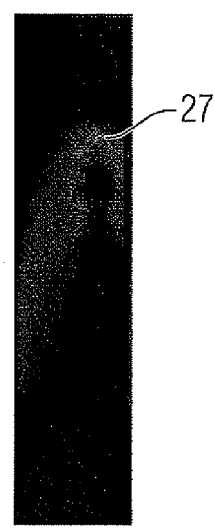

Finally, in accordance with FIGS. 9A and 9B, the global maximum is set to 0. Local maxima 26 and/or 27 remain. The angle and/or the distance from the image center for the positioning of the diaphragm results therefrom. In order to locate the local maxima, the global maximum is sought as the first local maximum, whereupon all pixels in a certain environment around this global maximum are set to 0. With a second search for the global maximum, the second local maximum is thus found. The end position for the semi-transparent diaphragm results by means of the local maximum, which is in the vicinity of the image center point and thus at the image recording center, with it being possible in turn to read off the distance from the image center point on the vertical axis in the Hough space.

Figure 10A:
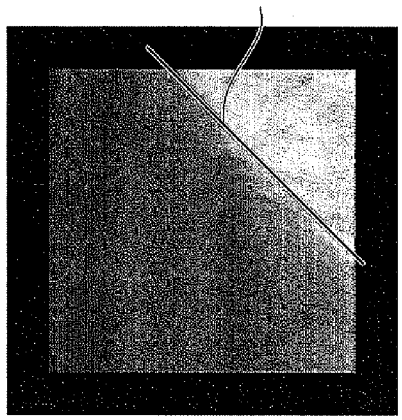
FIGS. 10A and 10B show the determined position for the semi-transparent diaphragm in the image recording and/or the image recording resulting with the moved-in diaphragm and FIG. 11 shows an inventive facility for determining a position for at least one semi-transparent diaphragm
Figure 10B:
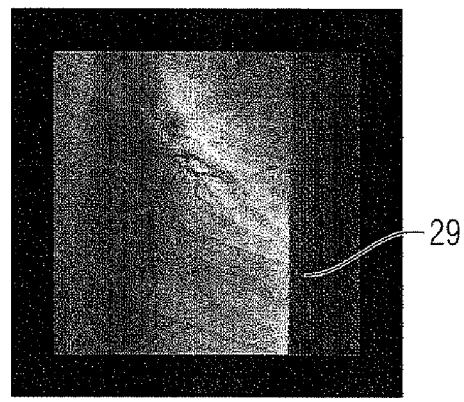

FIG. 10A finally shows the determined position 28 for a semi-transparent diaphragm in the image recording as claimed in FIG. 1A. FIG. 10b shows the resulting image recording 29 with the hitherto semi-transparent diaphragm which is moved-in at the optimal position. The image recording 29 does not have an interfering transition from regions of very large to regions of very low intensity. Overcontrolling of the image recording detector and the image system can thus be avoided. The image recording 29 has the quality which is necessary for an image-assisted monitoring in addition to an interventional measure.

Figure 11:
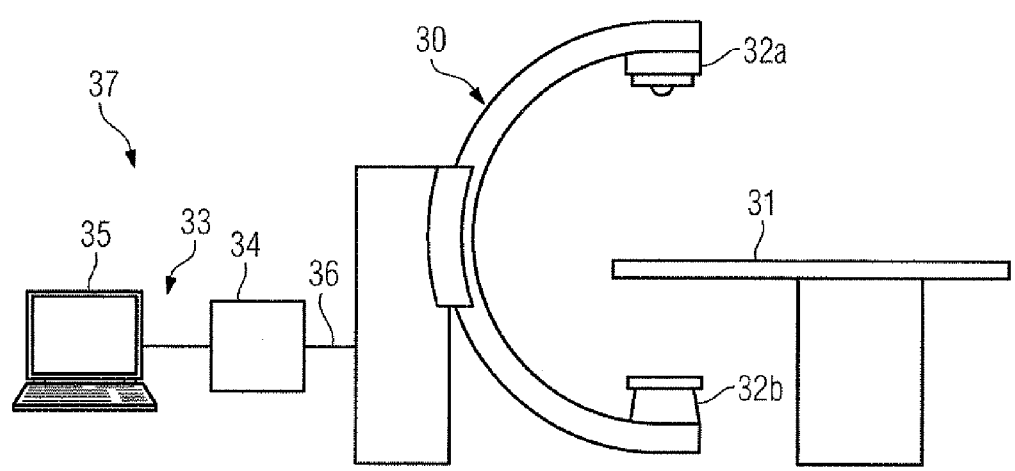

FIG. 11 shows an inventive facility 37 for determining a position for at least one semi-transparent diaphragm, which comprises a radiological facility 30, which is embodied as a C-arm system. A patient (not shown here) is arranged on the table 31 for the implementation of the interventional measure.

The radiological facility 30 comprises a radiation source and/or a detector 32a, 32b.

The radiological facility 30 is connected to a computing facility 33, which, in addition to a computing means 34, has an image output means 35 with a control facility.

The radiological facility 30 allows radiological image recordings to be produced, which are transmitted to the computing facility 33 by way of the connecting line 36. On the part of the computing means 34, the image recordings are analyzed in respect of identifying the less absorbent image regions, in order thus to automatically identify the suitable position for the arrangement of at least one semi-transparent diaphragm. To this end, the computing facility 33 has an automatic image processor in the form of a suitable software package.

An operator (not shown) also specifies instructions for the analysis of the image recordings with the aid of the image output means 35 using the control facility, in respect for instance of the edge filter to be used or the algorithm to be used with the elimination of edges produced by regular superimposition. Incidentally, the computing unit 33 of the facility 37 operates automatically to determine a position for a semi-transparent diaphragm. As a function of the position determined on the part of the computing means 34 for the semi-transparent diaphragm, this is arranged at the optimal position for the image observation with the aid of actuators (not shown here). A manual positioning of the semi-transparent diaphragm and/or several diaphragms (not shown here) is omitted. These are automatically positioned by way of actuators.

A user who handles image observation is thus able to concentrate totally on monitoring the quality of the image, which is available to the medical personnel for monitoring an intervention, without him/her having to additionally undertake the positioning of the semi-transparent diaphragm. On the other hand, a user who is simultaneously responsible for medical actions is able to focus totally on these actions, without having to take on an additional burden by virtue of the operational workload required for the manual positioning of the diaphragm.

The invention claimed is:

1. A method for positioning a semi-transparent diaphragm when radiologically observing a body region of a patient using a radiological device, the method comprising:
   producing an image recording of the body region using the radiological device;
   analyzing the image recording for identifying a less absorbent image region in the image recording; and
   determining a position for the semi-transparent diaphragm based on a result of the analysis;
   wherein the position for the semi-transparent diaphragm is adjusted by an actuator that is activated by a control device based on the determined position.

2. The method as claimed in claim 1, wherein the step of analyzing comprises:
   specifying a threshold value to binarize the image recording, and
   analyzing the binarized image recording in respect of an appearance of an edge between the less absorbent image region and a high absorbent image region.

3. The method as claimed in claim 2, wherein the image recording is morphologically filtered for eliminating a flaw or a gap after the binarization.

4. The method as claimed in claim 2, wherein the step of analyzing the binarized image recording comprises a step selected from the group consisting of:
   detecting the edge by an edge filter,
   eliminating an edge produced by a non-transparent diaphragm, and
   transforming the image recording in a Hough space.

5. The method as claimed in claim 4, wherein the edge is eliminated by deleting the edge that is parallel to an image border.

6. The method as claimed in claim 4, further comprising:
   low pass filtering the transformed image recording by a Hough transformation,
   searching for a local maxima in the transformed image recording, and
   determining the position for the semi-transparent diaphragm based on the local maxima.

7. The method as claimed in claim 4, wherein a straight line or a straight line segment is identified by a fit method.

8. The method as claimed in claim 1, wherein the position for the semi-transparent diaphragm is determined based on an image recording comprising a semi-transparent diaphragm that is at least partially moved into the image recording or is not moved into the image recording.

9. The method as claimed in claim 1, wherein the position for the semi-transparent diaphragm is determined based on a dynamic sequence of image recordings.

10. The method as claimed in claim 1, wherein the position for the semi-transparent diaphragm is determined in real time.

11. The method as claimed in claim 1, wherein the radiological observation is jointly performed with a cardiology.

12. The method as claimed in claim 1, wherein a sequence of image recordings of the body region are produced and the position for the semi-transparent diaphragm is determined for some image recordings of the sequence or within a scope of an average for a number of image recordings of the sequence.

13. The method as claimed in claim 12, wherein a change in the position over the sequence is at least partially filtered out.

14. The method as claimed in claim 1, wherein the image recording is analyzed based on a user specification.

15. The method as claimed in claim 1, wherein the observation accompanies with an interventional measure of the body region of the patient.

16. The method as claimed in claim 1, wherein the image recording is analyzed by an automatic image processing.

17. The method as claimed in claim 1, wherein the position is automatically determined.

18. A device for positioning a semi-transparent diaphragm when radiologically observing a body region of a patient, the device comprising:
 a radiological device that produces an image recording of the body region; and
 a computing device that analyzes the image recording to identify a less absorbent image region in the image recording and to determine a position for the semi-transparent diaphragm based on a result of the analysis;
 wherein the semi-transparent diaphragm is automatically moved to the determined position by an actuator controlled by the computing device.

19. The method as claimed in claim 1, wherein the position for the semi-transparent diaphragm is determined by the following steps performed by a computing device in the following sequence:

binarizing the image by setting pixels therein above a threshold value to a first binary value and setting pixels therein below the threshold value to a second binary value;

eliminating flaws and gaps in the binarized image by morphological filtering;

defining edges in the image by setting pixels only at points where a transition between the first and second binary values occurs in the binarized filtered image;

eliminating ones of the edges that parallel a border of the image;

producing a Hough space by performing a Hough transformation on a non-eliminated one of the edges;

determining the position for the semi-transparent diaphragm by selecting a maximum in the Hough space; and automatically positioning the semi-transparent diaphragm to the determined position via the actuator controlled by the computing device.

* * * * *